(12) United States Patent
Sarkas et al.

(10) Patent No.: US 10,555,892 B1
(45) Date of Patent: Feb. 11, 2020

(54) FUNCTIONALIZED SILOXANE OR POLYSILOXANE COATED PARTICLES WITH ENHANCED LIGHT FILTERING PROPERTIES

(71) Applicant: NANOPHASE TECHNOLOGIES CORPORATION, Romeoville, IL (US)

(72) Inventors: Harry W. Sarkas, Shorewood, IL (US); Anna Pavlovic, Elmwood Park, IL (US); Kevin Cureton, Evanston, IL (US); Harold G. Judd, Naperville, IL (US)

(73) Assignee: Nanophase Technologies Corporation, Romeoville, IL (US)

( * ) Notice: Subject to any disclaimer, the term of this patent is extended or adjusted under 35 U.S.C. 154(b) by 0 days.

(21) Appl. No.: 15/917,470

(22) Filed: Mar. 9, 2018

Related U.S. Application Data

(60) Provisional application No. 62/469,347, filed on Mar. 9, 2017, provisional application No. 62/504,418, filed on May 10, 2017.

(51) Int. Cl.
*A61K 8/89* (2006.01)
*A61K 8/06* (2006.01)
*A61C 17/06* (2006.01)

(52) U.S. Cl.
CPC ............... *A61K 8/89* (2013.01); *A61C 17/04* (2013.01); *A61K 8/062* (2013.01); *A61K 8/064* (2013.01); *A61K 2800/412* (2013.01); *A61K 2800/413* (2013.01)

(58) Field of Classification Search
CPC .... A61K 8/69; A61K 8/062; A61K 2800/412; A61K 2800/413; A17Q 17/04
See application file for complete search history.

(56) References Cited

U.S. PATENT DOCUMENTS

| | | |
|---|---|---|
| 2,885,366 A | 5/1959 | Iler |
| 2,938,009 A | 5/1960 | Lucas |
| 3,024,126 A | 3/1962 | Brown |
| 3,437,502 A | 4/1969 | Werner |
| 3,562,153 A | 2/1971 | Tully et al. |
| 3,635,743 A | 1/1972 | Smith |
| 3,647,742 A | 3/1972 | Stevens, Jr. |
| 3,649,588 A | 3/1972 | Kennedy-Skipton |
| 3,671,484 A | 6/1972 | Cooper et al. |
| 3,816,152 A | 6/1974 | Yates |
| 3,849,152 A | 11/1974 | Mimeault |
| 3,905,936 A | 9/1975 | Hawthorne |
| 3,920,865 A | 11/1975 | Laufer et al. |
| 3,948,676 A | 4/1976 | Laufer |
| 4,061,503 A | 12/1977 | Berger et al. |
| 4,068,024 A | 1/1978 | Laufer |
| 4,141,751 A | 2/1979 | Moreland |
| 4,151,154 A | 4/1979 | Berger |
| 4,233,366 A | 11/1980 | Sample, Jr. et al. |
| 4,243,692 A | 1/1981 | Scholze et al. |
| 4,271,234 A | 6/1981 | Schonafinger et al. |
| 4,454,288 A | 6/1984 | Lee et al. |
| 4,556,175 A | 12/1985 | Motoyama et al. |
| 4,574,082 A | 3/1986 | Tietjen et al. |
| 4,644,077 A | 2/1987 | Gupta |
| 4,781,942 A | 11/1988 | Leyden et al. |
| 4,818,614 A | 4/1989 | Fukui et al. |
| 4,845,054 A | 7/1989 | Mitchener |
| 4,877,604 A | 10/1989 | Schlossman |
| 4,882,225 A | 11/1989 | Fukui et al. |
| 4,927,464 A | 5/1990 | Cowie |
| 5,035,803 A | 7/1991 | Cohen |
| 5,063,254 A | 11/1991 | Nakos |
| 5,068,056 A | 11/1991 | Robb |
| 5,070,175 A | 12/1991 | Tsumura et al. |
| 5,143,722 A | 9/1992 | Hollenberg et al. |
| 5,274,064 A | 12/1993 | Sarkar |
| 5,277,888 A | 1/1994 | Baron et al. |
| 5,310,578 A | 5/1994 | Thurn-Muller et al. |
| 5,328,683 A | 7/1994 | Harashima |
| 5,348,760 A | 9/1994 | Parker et al. |
| 5,411,761 A | 5/1995 | Inokuchi et al. |

(Continued)

FOREIGN PATENT DOCUMENTS

| | | |
|---|---|---|
| AU | 2005229834 | 7/2008 |
| AU | 2005229834 | 1/2009 |

(Continued)

OTHER PUBLICATIONS

Jun. 23, 2010, U.S. Appl. No. 11/923,169, US.
Sep. 29, 2009, U.S. Appl. No. 11/923,169, US.
Jul. 26, 2007, U.S. Appl. No. 11/076,128, US.
Oct. 2, 2006, U.S. Appl. No. 11/076,128, US.
Jul. 15, 1998, U.S. Appl. No. 08/827,229, US.
Apr. 13, 1999, U.S. Appl. No. 08/827,229, US.
Oct. 7, 1999, U.S. Appl. No. 08/827,229, US.
Aug. 10, 1998, U.S. Appl. No. 08/954,396, US.
Jul. 26, 1999, U.S. Appl. No. 08/954,396, US.
May 6, 1999, U.S. Appl. No. 08/954,396, US.
Jul. 29, 1999, U.S. Appl. No. 08/954,396, US.
Nov. 12, 2013, U.S. Appl. No. 13/301,628, US.

(Continued)

*Primary Examiner* — Carlos A Azpuru
(74) *Attorney, Agent, or Firm* — Evan Law Group LLC

(57) ABSTRACT

A coated powder comprises (a) particles, and (b) a coating, on the surface of the particles. The surface coating comprises (1) optionally silica moieties, (2) organo oxysilane moieties selected from the group consisting of mono-organo oxysilane moieties, bi-organo oxysilane moieties and tri-organo oxysilane moieties, and (3) optionally organo-substituted polysiloxane moieties. The organo oxysilane moieties each have the formula $R'_n SiO_{4-n}$, with n=1, 2 or 3, and each R' group is independently selected from the group consisting of alkyl, alkenyl, alkynyl, esters, amides, and at least one aromatic moiety having an absorption band maximum in the region of 280 nm to 780 nm.

15 Claims, No Drawings

(56) References Cited

U.S. PATENT DOCUMENTS

| | | | |
|---|---|---|---|
| 5,440,001 A | 8/1995 | Griswold et al. | |
| 5,486,631 A | 1/1996 | Mitchnick et al. | |
| 5,536,492 A | 7/1996 | Mitchnick et al. | |
| 5,562,897 A | 10/1996 | Mitchnick et al. | |
| 5,565,591 A | 10/1996 | Mitchnick et al. | |
| 5,607,994 A | 3/1997 | Tooley et al. | |
| 5,631,310 A * | 5/1997 | Tooley | B82Y 30/00 523/212 |
| 5,674,624 A | 10/1997 | Miyazaki et al. | |
| 5,679,402 A | 10/1997 | Lee | |
| 5,718,907 A | 2/1998 | Labarre | |
| 5,756,788 A | 5/1998 | Mitchnick et al. | |
| 5,843,525 A | 12/1998 | Shibasaki et al. | |
| 5,868,959 A | 2/1999 | Mayo et al. | |
| 5,959,004 A | 9/1999 | Tooley et al. | |
| 5,993,967 A * | 11/1999 | Brotzman, Jr. | C09C 3/12 252/363.5 |
| 6,022,404 A | 2/2000 | Ettlinger et al. | |
| 6,033,781 A | 3/2000 | Brotzman, Jr. et al. | |
| 6,045,650 A | 4/2000 | Mitchnick et al. | |
| 6,066,327 A | 5/2000 | Gubernick et al. | |
| 6,086,668 A | 7/2000 | Farneth et al. | |
| 6,177,414 B1 | 1/2001 | Tomalia et al. | |
| 6,214,106 B1 | 4/2001 | Weber et al. | |
| 6,500,415 B2 | 12/2002 | Ishii et al. | |
| 6,599,631 B2 | 7/2003 | Kambe et al. | |
| 7,052,777 B2 | 5/2006 | Brotzman, Jr. et al. | |
| 7,182,938 B2 | 2/2007 | Andre et al. | |
| 7,303,819 B2 | 12/2007 | Brotzman, Jr. | |
| 7,407,666 B2 | 8/2008 | Tarletsky et al. | |
| 7,438,836 B2 | 10/2008 | Michael et al. | |
| 7,723,443 B1 | 5/2010 | O'Lenick et al. | |
| 7,790,813 B2 | 9/2010 | O'Lenick et al. | |
| 7,915,330 B2 | 3/2011 | Bonda et al. | |
| 9,139,737 B1 * | 9/2015 | Shah | C09C 3/12 |
| 9,657,183 B2 * | 5/2017 | Shah | C09C 3/12 |
| 2005/0222325 A1 | 10/2005 | Brotzman, Jr. | |
| 2005/0255057 A1 | 11/2005 | Andre et al. | |
| 2006/0167138 A1 | 7/2006 | Ishii et al. | |
| 2006/0210495 A1 | 9/2006 | Meyer et al. | |
| 2008/0057130 A1 | 3/2008 | Brotzman, Jr. | |
| 2016/0040019 A1 | 2/2016 | Shah et al. | |
| 2017/0283628 A1 | 10/2017 | Shah et al. | |
| 2018/0291210 A1 | 10/2018 | Sarkas et al. | |

FOREIGN PATENT DOCUMENTS

| | | |
|---|---|---|
| CA | 2010790 | 2/1990 |
| CA | 2563085 | 3/2013 |
| CA | 2563085 | 11/2013 |
| DE | 2828659 | 2/1979 |
| EP | 0 389 138 | 9/1990 |
| EP | 0 558 032 | 2/1993 |
| EP | 0 665 004 | 8/1995 |
| EP | 97 919 963.5 | 4/1999 |
| EP | 97 919 963.5 | 1/2001 |
| EP | 97 919 963.5 | 5/2003 |
| EP | 0 761 774 | 7/2003 |
| EP | 05760444.9 | 5/2009 |
| EP | 2 141 205 | 1/2010 |
| EP | 09168614.7 | 6/2010 |
| EP | 05760444.9 | 4/2011 |
| EP | 05 760 444.9 | 7/2014 |
| EP | 05 760 444.9 | 5/2016 |
| EP | 05760444.9 | 1/2017 |
| EP | 15 754 058.4 | 1/2018 |
| EP | 15754058.4 | 6/2018 |
| EP | 18162675.5 | 3/2019 |
| GB | 785393 | 10/1957 |
| GB | 825404 | 12/1959 |
| GB | 2217987 | 11/1989 |
| IN | 201827005834 | 5/2019 |
| JP | 62-016408 | 1/1987 |
| JP | 03-081209 | 4/1991 |
| JP | 4-178428 | 6/1992 |
| JP | 5-221640 | 8/1993 |
| JP | 5-306338 | 11/1993 |
| JP | 06-087714 | 3/1994 |
| JP | 6-279589 | 10/1994 |
| JP | 7-157562 | 6/1995 |
| JP | 7-165921 | 6/1995 |
| JP | 9-536259 | 11/2004 |
| JP | 9-536259 | 5/2006 |
| JP | 2006-248645 | 4/2008 |
| JP | 2007-507365 | 12/2009 |
| WO | 1990/06103 | 6/1990 |
| WO | 1990/09777 | 9/1990 |
| WO | 1995/23192 | 8/1995 |
| WO | PCT/US97/05179 | 8/1997 |
| WO | 1997/38041 | 10/1997 |
| WO | PCT/US97/05179 | 3/1998 |
| WO | 2005/098910 | 10/2005 |
| WO | PCT/US05/10669 | 12/2006 |
| WO | PCT/US05/10669 | 2/2008 |
| WO | 2009/131910 | 10/2009 |
| WO | PCT/US2015/042317 | 4/2016 |
| WO | 2017/019026 | 2/2017 |
| WO | PCT/US2015/042317 | 2/2018 |
| WO | PCT/US2018/026855 | 7/2018 |

OTHER PUBLICATIONS

Apr. 10, 2014, U.S. Appl. No. 13/301,628, US.
Jan. 27, 2015, U.S. Appl. No. 13/301,628, US.
Jun. 1, 2015, U.S. Appl. No. 13/301,628, US.
May 14, 2015, U.S. Appl. No. 13/301,628, US.
May 3, 2016, U.S. Appl. No. 14/827,155, US.
Jan. 11, 2017, U.S. Appl. No. 14/827,155, US.
Feb. 7, 2017, U.S. Appl. No. 14/827,155, US.
Mar. 30, 2018, U.S. Appl. No. 15/483,669, US.
Jun. 12, 2018, U.S. Appl. No. 15/491,913, US.
Sep. 14, 2018, U.S. Appl. No. 15/483,669, US.
U.S. Appl. No. 15/491,913, filed Apr. 19, 2017.
U.S. Appl. No. 15/483,669, filed Apr. 10, 2017.
U.S. Appl. No. 15/678,808, filed Aug. 16, 2017.
Jacobsen, A.E. et al., "Titanium dioxide pigments: Correlation between photochemical reactivity and chalking", Industrial and Engineering Chemistry, vol. 41, No. 3, pp. 523-526, (1949).
Brinker, et al., "Sol-Gel Science, the physics and chemistry of sol-gel processing", Academic press, chapters 3 and 4, pp. 97-301, (1990).
Supplementary European Search Report in corresponding European Patent Application No. 05760444.9-2011, dated May 15, 2009.
International Search Report dated Dec. 5, 2006 for PCT Application No. PCT/US05/10669.
Kinsley, Jr., G.R. "Properly purge and inert storage vessels", Chemical Engineering Progress, vol. 97, No. 2, pp. 57-61, (2001).
Baldyga, J. et al., "Effects of fluid motion and mixing on particle agglomeration and coating during precipitation", Chemical Engineering Science, vol. 60, issues 8-9, pp. 2167-2178, (2005).
Solomon, D.H. et al., "Titania Pigments" "Surface modification of pigments and fillers" "Organic reactions catalyzed by mineral surfaces", chemistry of Pigments and Fillers, John Wiley & Sons, (1983).
International Search Report dated Aug. 4, 1997 for PCT Application No. PCT/US97/05179.
International Cosmetic Ingredient Dictionary, $5^{th}$ edition, Published by the Cosmetic, Toiletry, and Fragrance Association, vol. 1, p. 401, (1993).
International Cosmetic Ingredient Dictionary, $5^{th}$ edition, Published by the Cosmetic, Toiletry, and Fragrance Association, vol. 1, pp. 649-650, (1993).
International Cosmetic Ingredient Dictionary, $5^{th}$ edition, Published by the Cosmetic, Toiletry, and Fragrance Association, vol. 2, p. 924, (1993).
Kingery, W.D. et al., "Introduction to Ceramics", $2^{nd}$ Edition, John Wiley & Sons, pp. 3, 16-20, (1976).
Rompp Lexikon Chemie, 10, Auflage, pp. 4564-4565, (1999).

(56) References Cited

OTHER PUBLICATIONS

Rompp Lexikon Chemie, 10, Auflage, pp. 5076, (1999).
Odian, G. "Principles of Polymerization", $2^{nd}$ Edition, John Wiley & Sons, pp. 238-239 400-401 424-425, (1981).
Billmeyer, Jr., F.W. Textbook of Polymer Science, Interscience Publishers, pp. 332-337, (1962).
Jastrzebski, Z.D. "Ceramics and Related Materials", Nature and Properties of Engineering Materials, John Wiley & Sons, Inc. p. 281, (1959).
Billmeyer, Jr., F.W. Textbook of Polymer Science, Interscience Publishers, p. 350, (1971).
Odian, G. "Principles of Polymerization", $2^{nd}$ Edition, John Wiley & Sons, pp. 429-430, (1981).
Flory, P.J. "Nonlinearity in the macro-structure of vinyl polymers", Principles of Polymer Chemistry, Cornell University Press, Chapter III and Chapter VI, section 4, pp. 69-105, 256-262, (1971).
Meakin, P. "Models for colloidal aggregation", Annual Reviews Physical Chemistry, vol. 39, pp. 237-267, (1988).
Brinker, et al., "Sol-Gel Science, The physics and chemistry of sol-gel processing", Academic press, chapters 1, pp. 1-8, (1990).
Kingery, W.D. et al., "Introduction to Ceramics", $2^{nd}$ Edition, John Wiley & Sons, pp. 61-71, (1976).
International Search Report and Written Opinion dated Apr. 28, 2016 for PCT Application No. PCT/US2015/042317.
International Search Report and Written Opinion dated Jul. 19, 2018 for PCT Application No. PCT/US2018/026855.
Jung, K. et al., "The antioxidative power AP—A new quantitative time dependent (2D) parameter for the determination of the antioxidant capacity and reactivity of different plants", Spectrochimica Acta Part A: Molecular and Biomolecular Spectroscopy, vol. 63, pp. 845-850, (2006).
Jung, K. et al., "How active are biocosmetic ingredients?", SÖFW-Journal, vol. 133, No. 1/2, pp. 1-7, (2007).
Andersch Björkman, Y. et al., "Air-oxidized linalool elicits eczema in allergic patients—a repeated open application test study", Contact Dermatitis, vol. 70, No. 3, pp. 129-138, (2014).
Jung, K. et al., "High levels of free radicals in suncare products induce acne aestivalis in sensitive subjects", SÖFW, vol. 142, pp. 2-8, (2016).
Wlaschek, M. et al., "Solar UV irradiation and dermal photoaging", Journal of Photochemistry and Photobiology B: Biology, vol. 63, issues 1-3, pp. 41-51, (2001).
Wada, N. et al., "Mycosporine-like amino acids and their derivatives as natural antioxidants", Antioxidants, vol. 4, pp. 603-646, (2015).
Vadlapudi, V. "Antioxidant activities of marine algae: A review", Medicinal Plants as Antioxidant Agents: Understanding Their Mechanism of Action and Therapeutic Efficacy, pp. 189-203, (2012).
Hanson, K.M. et al., "Bioconvertible vitamin antioxidants improve sunscreen photoprotection against UV-induced reactive oxygen species", Journal of Cosmetic Science, vol. 54, pp. 589-598, (2003).
Chisvert, A. et al., "An overview of the analytical methods for the determination of organic ultraviolet filters in biological fluids and tissues", Analytica Chimica Acta, vol. 752, pp. 11-29, (2012).
Leite-Silva et al., "Human skin penetration and local effects of topical nano zinc oxide after occlusion and barrier impairment", European Journal of Pharmaceutics and Biopharmaceutics, vol. 104, pp. 140-147, (2016).
Holmes, A.M. et al., "Relative penetration of zinc oxide and zinc ions into human skin after application of different zinc oxide formulations", ACS Nano, vol. 10, pp. 1810-1819, (2016).
Australian Government, "Literature review on the safety of titanium dioxide and zinc oxide nanoparticles in sunscreens", Department of Health, Therapeutic Goods Administration, Scientific Review Report, pp. 1-24, (2016).
EP Search Report dated Jul. 3, 2018 for EP application No. 18162675.5, 8 pages.
Matts, P.J. et al., "The COLIPA in vitro UVA method: a standard and reproducible measure of sunscreen UVA protection", International Journal of Cosmetic Science, vol. 32, issue 1, pp. 35-46, (2010).
International Standard, "Determination of sunscreen UVA photoprotection in vitro", ISO 24443, First edition, pp. 1-28, (2012).
Mar. 5, 2019, U.S. Appl. No. 15/491,913, US.
May 10, 2019, U.S. Appl. No. 15/483,669, US.
May 21, 2019, U.S. Appl. No. 15/491,913, US.
Aug. 6, 2019, U.S. Appl. No. 15/491,913, US.
Aug. 8, 2019, U.S. Appl. No. 15/483,669, US.

* cited by examiner

FUNCTIONALIZED SILOXANE OR POLYSILOXANE COATED PARTICLES WITH ENHANCED LIGHT FILTERING PROPERTIES

BACKGROUND AND GENERAL DESCRIPTION

The present invention is a class of coated particles (powders) where the coating is multifunctional and is distinguished from previous inventions in that it contains UVB, UVA, and visible light absorbers as well as stabilizers integrally grafted into the coating. The coating also contains elements which enhance the dispersion of the particles into common fluids and resins to support high solids loadings. In another aspect of this invention, the coating can impart photostability (substantial reduction of photoreactivity) in the cases where the base particles are light absorbers themselves.

The coated particles of the present invention are suitable for use in any particle-loaded system where light absorption is desired (e.g. photo-protection applications), but have particular utility in topical sunscreen applications. The most advantageous molecules to be integrally grafted into the coating are thought to be common organic UVB absorbers, UVA absorbers and light stabilizers commonly employed in topical sunscreen applications.

A notable deficiency of organic UVB absorbers, UVA absorbers and light stabilizers used in sunscreen is absorption through the skin, which is associated with these species being small molecules. A number of studies have now shown that such organic UV filters can be absorbed through the skin after topical application where they may be metabolized, excreted, or bioaccumulated. Following absorption into the skin, the presence of these molecules may have deleterious effects caused by the generation of free radicals (genotoxicity) or may also be associated with the endocrine disruption. This information is discussed in detail A. Chisvert et al. Analytica Chimica Acta 752, 11-29 (2012).

One of the advantages of the present invention is that it allows for the efficient protective action of organic UV filters and stabilizers while preventing them from absorbing into the skin since they are anchored to a particle via incorporation into the coating. It has now been demonstrated in several studies that particles, even nanoparticles, do not penetrate human skin and that the stratum corneum is an effective barrier to penetration. See V. R. Leite-Silva et al. European Journal of Pharmaceutics and Biopharmaceutics 104, 140-147 (2016); A. M. Holmes et al. ACS Nano 10, 1810-1819 (2016); and Australia TGA 2016 *Literature Review on the safety of titanium dioxide and zinc oxide nanoparticles in sunscreens.*

A further aspect of this invention takes advantage of substantial reduction in photoreactivity that the coating imparts to the coated base particle in the case where the particle is a light absorber (wide band gap semiconductor). This is accomplished by suppression of free radical species that are normally generated following photo-excitation of a wide band gap semiconductor particle. The suppression (quenching) of these free radical species prevents the free radical attack on susceptible species, such as antioxidants, that would normally follow light absorption. This absence of photo-generated radicals as well as the photo-protective action of the coated powder of the present invention on antioxidant molecules, in effect, boosts the activity of these species by preventing their degradation or deactivation.

The invention claims the compositions of the coated powders, solid and liquid dispersions incorporating the coated particles (powders), sunscreen and cosmetic formulations incorporating the coated particles (powders), method of protecting human skin and keratinous materials through the use of the coated particles, method of protecting photosensitive active ingredients (antioxidants) through the use of the coated particles, and the skin health benefits associated with enhancing the activity of photosensitive active ingredients (antioxidants).

It should be noted that while the compositions of the present invention have not been synthesized to date, methods of synthesizing said compositions are described in detail below employing well-known chemical synthetic routes that would be understood by one of ordinary skill in the art.

DESCRIPTION OF THE INVENTION

The present invention describes a special class of multifunctional coated particles that are related to the compositions disclosed in U.S. Pat. No. 9,139,737, and U.S. patent application Ser. Nos. 14/827,155 and 15/483,669.

The essential elements of the compositions remain:
A coated powder comprising:
(a) particles, and
(b) a coating, on the surface of the particles, comprising
  (1) silica moieties,
  (2) organo oxysilane moieties selected from the group consisting of mono-organo oxysilane moieties, bi-organo oxysilane moieties and tri-organo oxysilane moieties, and
  (3) organo-substituted polysiloxane moieties In all embodiments of the present invention, the silica moieties remain as in previous cases.

In one embodiment of the present invention the organo oxysilane moieties contain at least one functional group comprising an aromatic moiety having an absorption band maximum in the region of 280 nm to 780 nm. This is accomplished by attaching the moiety as a pendant group on the silane via a linkage that is described in more detail later in this disclosure. Most commonly, the moieties of interest have strong absorption bands in the UVA and UVB spectral regions, although these absorption bands may occur in the visible region of the electromagnetic spectrum as well. Common absorbing moieties include, but are not limited to: benzophenone-3, benzophenone-4, benzophenone-5, benzophenone-8, 3-benzylidene camphor, bis-ethylhexyloxyphenol methoxyphenyl triazine, butyl methoxydibenzoylmethane, camphor benzalkonium methosulfate, diethylamino hydroxybenzoyl hexyl benzoate, diethylhexyl butamido triazone, disodium phenyl dibenzimidazole tetrasulfonate, drometrizole trisiloxane, ethoxyethyl methoxycinnamate, ethylhexyl salicylate, ethylhexyl triazone, homosalate, isoamyl p-methoxycinnamate, methyl anthranilate, 4-methylbenzylidene camphor, methylene bis-benzotriazoyl tetramethylbutylphenol, octocrylene, methoxycrylene, para aminobenzoic acid, PEG-25 para aminobenzoic acid, phenylbenzimidazole sulfonic acid, polyacrylamide methylbenzylidene camphor, triethanolamine salicylate, terephthalylidene dicamphor sulfonic acid, and benzylidene camphor sulfonic acid. Mixtures of these absorbing moieties may also be incorporated into the coating via the organosilane moieties.

Reactive silanes which may be used to incorporate the organo oxysilane moieties containing at least one functional group comprising an aromatic moiety having an absorption band maximum in the region of 280 nm to 780 nm are commercially available. One example is 2-hydroxy-4-(3- triethoxysilylpropoxy) diphenyketone, (CAS No. 79876-59-8) supplied by Gelest Inc. (Product Code SIH6200.0).

In this embodiment, the organo-substituted polysiloxane moieties may be dialkyl substituted polysiloxanes as in the previous cases.

The particles in these compositions include nanoparticles but are not limited to particles below 1000 nm. Common pigment particles having averages sizes above 1000 nm may also comprise these compositions. Such materials include $Fe_2O_3$, FeOOH, ZnO, $TiO_2$, and BiOCl. Further compositions may include silica, talc, kaolin, mica, synthetic fluorophogopite, and the like.

The present invention also contains the subset of materials detailed in U.S. patent application Ser. No. 15/483,669 comprising coated powder wherein $SiO_2$ residues derived from the combination of the silica moieties and the mono-organo oxysilane moieties, bi-organo oxysilane moieties and tri-organo oxysilane moieties is greater than or equal to 0.0625% of the total coated powder weight per $m^2/g$ of specific surface area of the nanoparticle. This is particularly advantageous in cases where the coated powders are themselves UVA or UVB absorbers such as ZnO and $TiO_2$. Light absorbing particles in this class are known to generate free radicals upon light excitation. These free radicals may damage the UV absorbing aromatic moieties incorporated into the coating. It is therefore desirable to select a coating composition as described in U.S. patent application Ser. No. 15/483,669 that prevents the formation of radical species beyond the physical boundary of the particle.

In another embodiment of the present invention, the functional groups comprising aromatic moieties having an absorption band maximum in the region of 280 nm to 780 nm are incorporated into the coating via the organo-substituted polysiloxane moieties. In this embodiment, the organo-substituted polysiloxane moieties differ from those of our previous inventions, which were only dialkyl substituted. In the present invention, the organo-substituted polysiloxane moieties may be branched in addition to containing the light absorbing moieties. The generalized preferred organo polysiloxane structure for this embodiment is shown below:

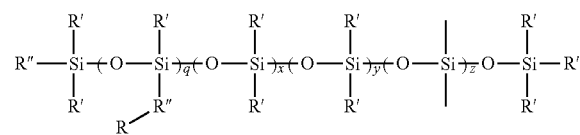

R = H, OH, SH, aryl including UV absorbing moiety from 280-780 nm; 1', 2'', 3'''-amines, esters
R' = $CH_3$; $CH_3O$; $C_2H_5O$; alkoxy with branched or linear carbon chain from C3-C30
R'' = Branched or linear alkyl group C1 up to C30; polyethylene oxide $(C_2H_4O)_{m=1-100}$; polypropylene oxide $(C_3H_6O)_{m=1-100}$
$q$ = from 0 to 1000 - $(x+y+z)$
$x$ = from 0 to 1000 - $(q+y+z)$
$y$ = from 0 to 1000 - $(q+x+z)$
$z$ = From 0 to 1000 - $(q+x+y)$
$q+x+y+z$ = 1 up to 1000

This structure allows pendant groups to be added along the backbone of the polysiloxane moiety and also provides reactive groups for the complete, substituted polysiloxane moiety to be reacted (cross-linked) into the overall coating composition.

Reactive organo-substituted polysiloxane moieties of the structure shown above may be produced through hydrolysis and subsequent polymerization of reactive silanes using the method described in U.S. Pat. No. 3,373,138 where alkoxysilane precursors may be hydrolyzed according to U.S. Pat. No. 4,395,563 prior to polymerization. These structures may be formed from either pure hydrolysates of reactive silanes or mixtures of hydrolysates of reactive silanes according to the desired composition. One example is a polymer formed from the hydrolysate of 2-hydroxy-4-(3-triethoxysilylpropoxy) diphenyketone. An example of a mixture is the polymer formed from the mixed hydrolysates of 2-hydroxy-4-(3-triethoxysilylpropoxy) diphenyketone and triethoxy (octyl) silane.

Another approach for producing the reactive organo-substituted polysiloxane moieties of the structure shown above involves grafting the functional group(s) comprising an aromatic moiety having an absorption band maximum in the region of 280 nm to 780 nm to a pre-formed reactive organo-substituted polysiloxane having suitable reactive groups for coupling reactions. Organo-substituted polysiloxanes (without light absorbing pendant groups) suited to this approach are commercially available through Siltech Corporation under the Silmer line of reactive silicones. Some of these compositions are described in U.S. Pat. Nos. 7,407,666, 7,723,443, 7,790,813. And U.S. Pat. No. 5,486,631. Siltech offers ten classes of reactive silicones 1. Silmer OH (hydroxyl functional), 2. Silmer OHT (dual hydroxyl functional), 3. Silmer ACR (acrylate functional), 4. Silmer OH ACR (acrylate functional with secondary hydroxyl functionality), 5. Silmer H (hydride functional), 6. Silmer NCO (isocyanate functional), 7. Silmer NH (amino functional), 8. EP, 9. Silmer VIN (vinyl functional), and 10. Silmer TMS (trimethoxysilane functional). Siltech also offers customizable homologues and combinations of these functionalized reactive silicones that can be used to produce the organo-substituted polysiloxane moieties with grafted light absorbing pendant groups of the present invention. The TMS, OH, H, and VIN versions of these pre-polymers are thought to be the most useful raw materials for the present invention.

Two enabling examples of octocrylene substitution into the backbone of a reactive organo polysiloxane that may be incorporated into the present invention taking two different synthetic approaches are illustrated below.

In the first approach, the primary silicone backbone is first prepared containing functionalized pendants, such as hydrogen or vinyl groups. The desired pendant group is then grafted onto the backbone. The example shows octocrylene substituted with a hydrocarbon chain terminated with a reactive vinyl group. This group then reacts with the silicon hydride group on the polysiloxane via addition reaction to yield the organo substituted polysiloxane. The resultant organo substituted polysiloxane shown can then be reacted into the coating structure via the methoxy end-block groups in the same manner taught in our original applications. Alternatively, the polysiloxane may be functionalized with a vinyl group instead of a hydride, and the grafting could proceed through the well-known olefin metathesis reaction. In practice, any convenient or economically preferred reaction could be used in this grafting approach.

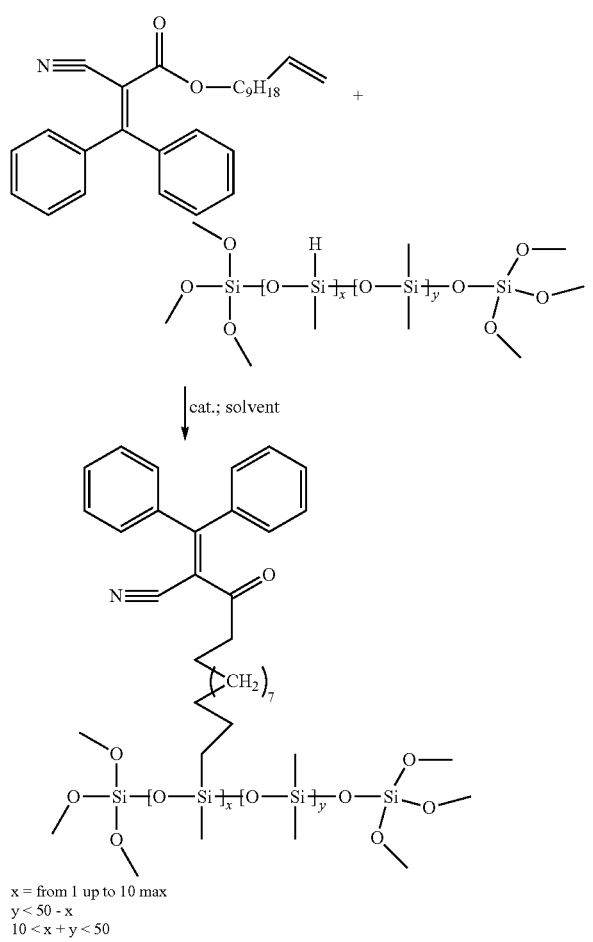

$x$ = from 1 up to 10 max
$y < 50 - x$
$10 < x + y < 50$

In the second approach, the desired pendant is first attached to a silicon mer and the desired pendant then is blended with the reactive silicon mers and polymerized to give the final substituted polysiloxane. An example of this approach is shown below again using the case of octocrylene as the light absorbing moiety. This case is illustrated below.

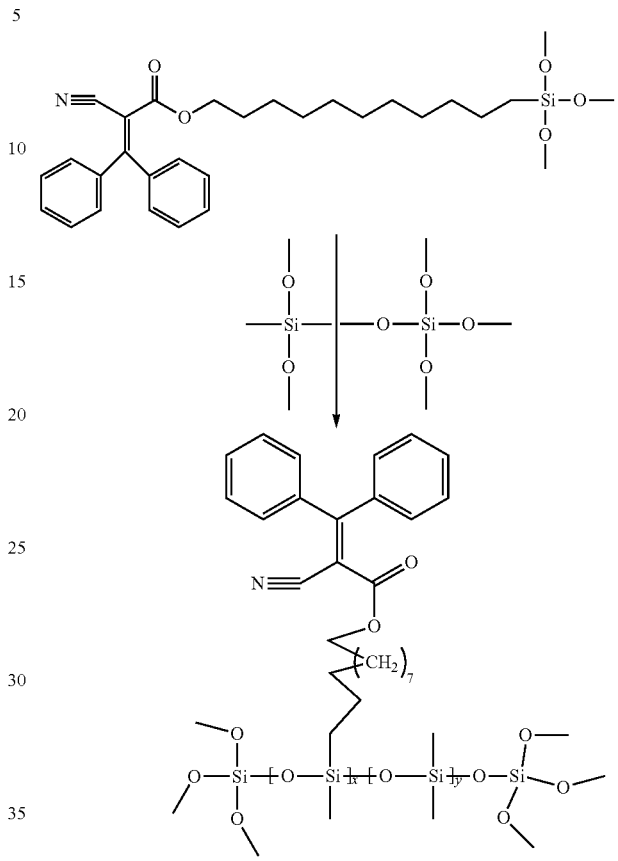

In this second approach, it is not necessary to have reactive silicone pre-polymers as in the first example above. Note that analogous reactions used in the second approach above may be used to synthesize the organo oxysilane moieties selected from the group consisting of mono-organo oxysilane moieties, bi-organo oxysilane moieties and tri-organo oxysilane moieties, since these reactive silanes substituted with the light absorbing functional groups of the present invention are generally not commercially available. This would be the approach taken to synthesize the coating in the first embodiment of this invention discussed earlier.

In a further aspect of the present invention, non-absorptive pendant groups may also be grafted into the backbone of the silicone pre-polymer before its incorporation into the coating. This may be advantageous to improve the dispersion of the coated particles into the host medium and/or to space the light absorbing pendant groups in order to prevent unwanted effects such as π-stacking, which could shift the spectral properties of the absorber moieties. An example of using an alkane pendant group together with a pendant group incorporating octocrylene is illustrated below.

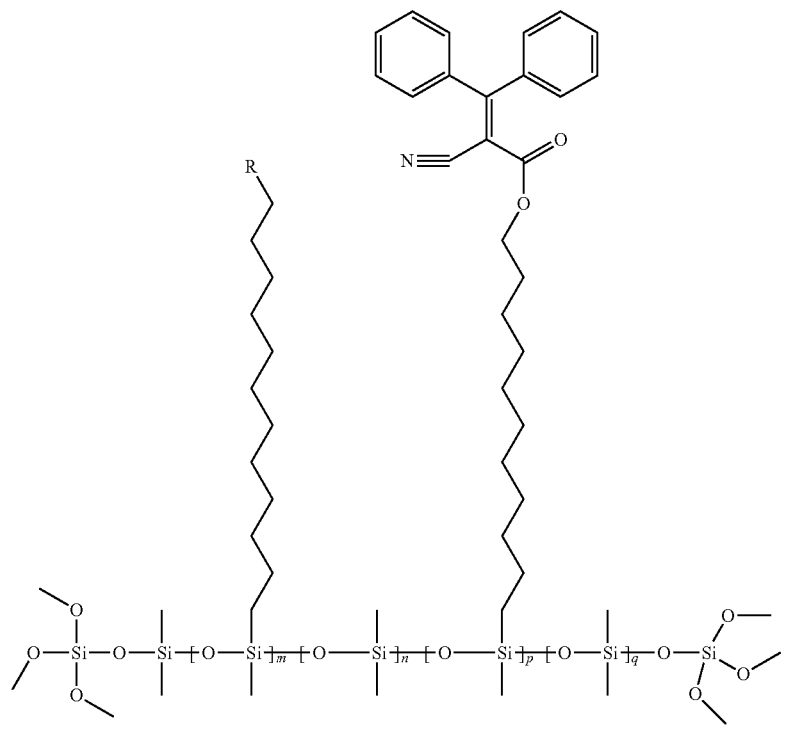

R = H, C₆H₁₂, C₈H₁₈
10 < m + n + p + q < 50
m = from 1 up to 10 max
p = from 1 up to 10
n + q < 50 - m - p EXAMPLE: ZnO (specific surface area=7 m²/g, corresponding average particle size=153 nm) was coated as follows: 92.7% ZnO, 4.7% $SiO_2$ from propylsilane moieties, 0.149% $SiO_2$ from silicate moieties, with the balance of $SiO_2$ moieties coming from an reactive organo-substituted polysiloxane of the type shown above where the alkyl substitution was in the form of behenyl groups and the crylene substitution was grafted to the silicone using a C11 alkyl moiety (which may be prepared by well-known methods, such as those described in U.S. Pat. No. 7,915,330). The resulted coated powder was dispersed in squalane at 80% powder solids to form a pourable dispersion. No dispersant was necessary.

One aspect of enabling the present invention is defining synthetic pathways for producing pendant groups for grafting into the organo oxysilane moieties and/or organo-substituted polysiloxane moieties that are well understood to those of ordinary skill in the art. The example below illustrates one possible synthetic approach where a crylene moiety is reacted through transesterification to yield a pendant octocrylene moiety with a terminal vinyl group that may be subsequently reacted with a silicon hydride group on a silane or silicone pre-polymer (organo-substituted polysiloxane) via addition reaction to graft the octocrylene moiety onto the reactive silane or silicone pre-polymer which is then further reacted into the overall coating composition of the invention.

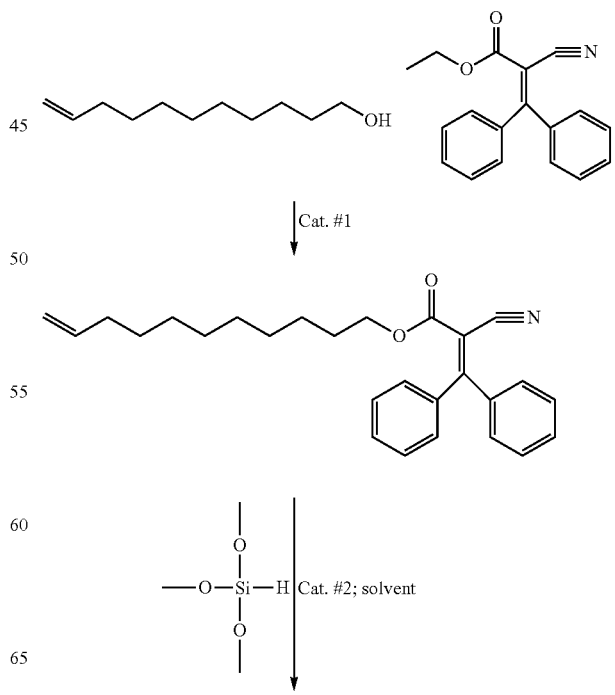

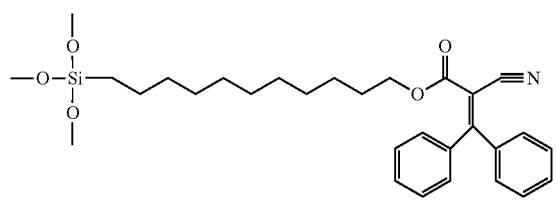

The examples given above using octocrylene as the light absorbing moiety are not limiting. Any light absorbing functional group meeting the requirements defined above, may be grafted into the components of the coating of the present invention.

The example below illustrates the synthesis of a diethylamino hydroxybenzoyl alkyl benzoate derivative with a terminal vinyl group, as before, for reacting into the organosilane and/or organo substituted polysiloxane constituents of the coating composition of the present invention.

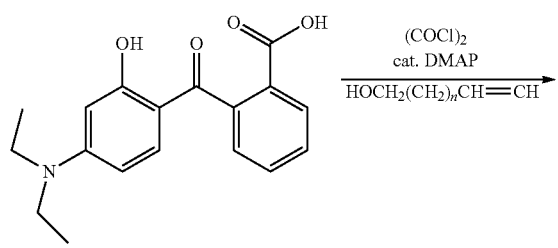

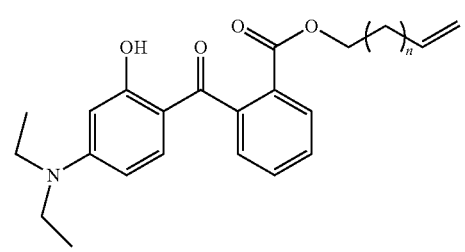

Functionalization for grafting into the organosilane and/or organo substituted polysiloxane constituents of the coating composition of the present invention is not limited to terminal vinyl groups. Reactive hydroxyl groups are also considered to be advantageous for grafting reactions. example below illustrates the synthesis of a diethylamino hydroxybenzoyl benzoate derivative functionalized with a polyethylene oxide chain which is terminated with a reactive hydroxyl group.

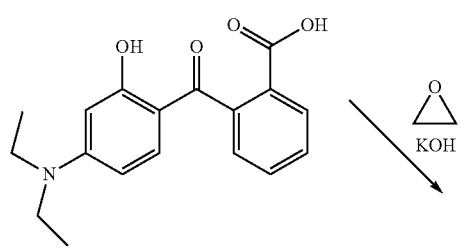

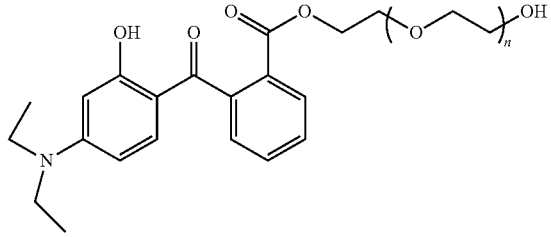

As shown below, benzophenone derivatives may also be functionalized for grafting in this manner.

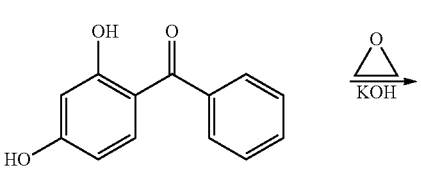

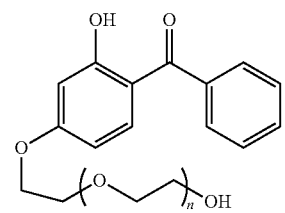

This approach is further exemplified by the synthetic pathway shown below, which illustrates the similar functionalization of a pheny benzimidazole for grafting into the organosilane and/or organo substituted polysiloxane constituents of the coating composition of the present invention.

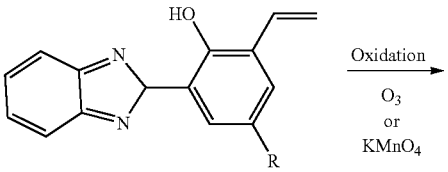

R = H, t-Bu, alkyl, alyoxy, etc

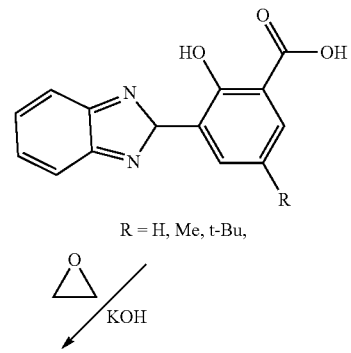

R = H, Me, t-Bu,

-continued

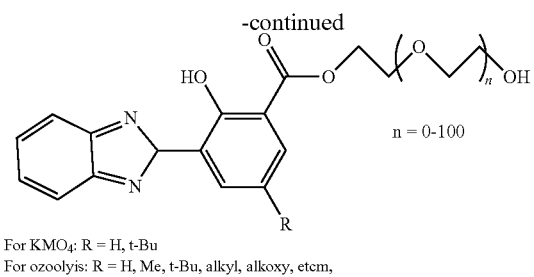

n = 0-100

For KMO₄: R = H, t-Bu
For ozoolyis: R = H, Me, t-Bu, alkyl, alkoxy, etcm,

As mentioned, any suitable absorber moiety, as defined, may be selected. Some final examples of advantageous moieties are the salicylate and cinnamate pendant groups illustrated below, respectively.

R₁ aryl groups defined:

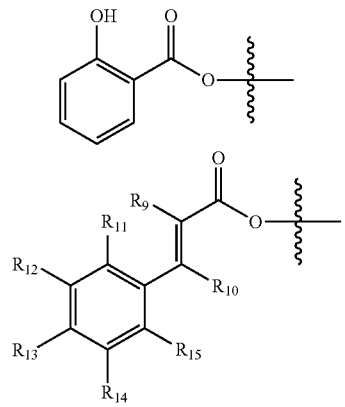

$R_9$ = H, CH₃—, —CN
$R_{10}$ = H, tBu, Phenyl, Naphthalate
$R_{11}$-$R_{15}$ = H, CH₃—, CH₃O—, C₂H₅O—, CH₂OH, —NH₂, —NHR₇, —NR₇R₈

The coating in the present invention is applied to the particles as in our previous inventions. A precursor for the silica moieties (typically tetraethoxy silane), the organo oxysilane(s) (typically with alkoxide reactive groups), and the organo-substituted polysiloxane(s) (typically with hydroxide or alkoxide reactive groups) are loaded into a sealed vessel with the powder (particles) to be coated. The mixture is blanketed with an inert gas and the temperature is raised to 90-120° C. for 1-3 hours. The fully reacted powder is then dried at 90-120° C. for 1-3 hours under a flow of inert gas or vacuum to remove residual materials (water and alcohols). The composition of the present invention is then cooled to room temperature and then discharged from the reaction vessel.

In yet another aspect of the present invention, the suppression (quenching) of free radical species prevents the free radical attack on both skin lipids and susceptible species, such as antioxidants, that would normally follow light absorption. This absence of photo-generated radicals as well as the photo-protective action of the coated powder of the present invention on antioxidant molecules, in effect, boosts the activity of these species. It is well established that the topical use of antioxidants can suppress lipid peroxidation and significantly reduce skin aging, resulting in improvement of overall skin health. Among the claimed benefits of topical application of formulas comprising the coated powders of the present invention are those associated with suppressing lipid peroxidation which include reducing skin lines and wrinkles, preventing loss of elasticity, and preventing skin thinning.

In an additional aspect of the present invention, the functional groups comprising aromatic moieties having an absorption band maximum in the region of 280 nm to 780 nm may be applied onto the surface of a particle to be coated either (1) via the organo oxysilane moieties wherein the additional incorporation of either or both the silica moieties and organo-substituted polysiloxane moieties are optional or (2) via the organo-substituted polysiloxane moieties wherein the additional incorporation of either or both the silica moieties and organo oxysilane moieties are optional.

The invention claimed is:

1. A coated powder comprising:
    (a) particles, and
    (b) a coating, on the surface of the particles, comprising
        optionally (1) silica moieties,
        (2) organo oxysilane moieties selected from the group consisting of mono-organo oxysilane moieties, bi-organo oxysilane moieties and tri-organo oxysilane moieties, and
        optionally (3) organo-substituted polysiloxane moieties
        wherein the organo oxysilane moieties each have the formula $R'_n SiO_{4-n}$, with n=1, 2 or 3, each R' group is independently selected from the group consisting of alkyl, alkenyl, alkynyl, esters, amides and aromatic moieties having an absorption band maximum in the region of 280 nm to 780 nm, and
    at least one organo oxysilane moiety comprises the aromatic moiety having an absorption band maximum in the region of 280 nm to 780 nm.

2. The coated powder of claim 1, wherein the particles comprise at least one oxide selected from the group consisting of zinc oxides, titanium oxides, silicon oxides, aluminum oxides, iron oxides, bismuth oxides, tin oxides, indium oxides, tungsten oxides, rare-earth metal oxides, and interference pigments.

3. The coated powder of claim 2, wherein the particles comprise at least one oxide selected from the group consisting of ZnO, TiO₂, SiO₂, Al₂O₃, Fe₂O₃, CeO₂, Bi₂O₃, antimony-tin oxide, indium-tin oxide, doped WO₃, and mixtures thereof.

4. The coated powder of claim 1, wherein the particles have an average particle size of 1-1000 nm.

5. The coated powder of claim 1, wherein SiO₂ residues formed during ignition of the coated powder derived from the combination of the silica moieties and the mono-organo oxysilane moieties, bi-organo oxysilane moieties and tri-organo oxysilane moieties is greater than or equal to 0.0625% of the total coated powder weight per m²/g of specific surface area of the nanoparticle.

6. The coated powder of claim 1 wherein the aromatic moieties having absorption band maxima in the region of 280 nm to 780 nm comprise a moiety corresponding to at least one selected from the group consisting of benzophenone-3, benzophenone-4 benzophenone-5, benzophenone-8, 3-benzylidene camphor, bis-ethylhexyloxyphenol methoxyphenyl triazine, butyl methoxydibenzoylmethane, camphor benzalkonium methosulfate, diethylamino hydroxybenzoyl hexyl benzoate, diethylhexyl butamido triazone, disodium phenyl dibenzimidazole tetrasulfonate, drometrizole trisiloxane, ethoxyethyl methoxycinnamate, ethylhexyl salicylate, ethylhexyl triazone, homosalate, isoamyl p-methoxycinnamate, methyl anthranilate, 4-methylbenzylidene camphor, methylene bis-benzotriazoyl tetramethylbutylphenol, octocrylene, methoxycrylene, para aminobenzoic acid, PEG-25 para aminobenzoic acid, phenylbenzimidazole sulfonic acid, polyacrylamide methylbenzylidene camphor, triethanolamine salicylate, terephthalylidene dicamphor sulfonic acid, and benzylidene camphor sulfonic acid.

7. A liquid dispersion comprising the coated powder of claim 1 suspended in a cosmetically acceptable carrier fluid.

8. An oil-in-water emulsion comprising the coated powder of claim 1.

9. A water-in-oil emulsion comprising the coated powder of claim 1.

10. An anhydrous sunscreen formulation comprising the coated powder of claim 1.

11. A method of protecting keratinous material comprising coating the keratinous material with a composition comprising the coated powder of claim 1.

12. A method of protecting human skin comprising coating skin with a composition comprising the coated powder of claim 1.

13. A coated powder comprising:
(a) particles, and
(b) a coating, on the surface of the particles, comprising optionally (1) silica moieties,
optionally (2) organo oxysilane moieties selected from the group consisting of mono-organo oxysilane moieties, bi-organo oxysilane moieties and tri-organo oxysilane moieties, and
(3) organo-substituted polysiloxane moieties
wherein the organo oxysilane moieties each have the formula $R'_n SiO_{4-n}$, with n=1, 2 or 3, and each R' group is independently, selected from the group consisting of alkyl, alkenyl, alkynyl, esters, and amides, and
wherein the organo-substituted polysiloxane moieties contain substituent groups comprising at least one aromatic moiety having an absorption band, maximum in the region of 280 nm to 780 nm.

14. A coated powder comprising:
(a) particles, and
(b) a coating, on the surface of the particles, comprising optionally (1) silica moieties,
(2) organo oxysilane moieties selected from the group consisting of mono-organo oxysilane moieties, bi-organo oxysilane moieties and tri-organo oxysilane moieties, and
(3) organo-substituted polysiloxane moieties
wherein the organo oxysilane moieties each have the formula $R'_n SiO_{4-n}$, with n=1, 2 or 3, and each R' group is independently selected from the group consisting of alkyl, alkenyl, alkynyl, esters, amides, and at least one aromatic moiety having an absorption band maximum in the region of 280 nm to 780 nm, and
the organo-substituted polysiloxane moieties contain substituent groups comprising at least one aromatic moiety having an absorption band maximum in the region of 280 nm to 780 nm.

15. A dry powder formulation comprising the coated powder of claim 1.

* * * * *